(12) United States Patent
Umezu et al.

(10) Patent No.: US 6,777,001 B1
(45) Date of Patent: Aug. 17, 2004

(54) METHOD OF PRODUCTION OF CERAMICS

(75) Inventors: Yoshikazu Umezu, Tokorozawa (JP); Takehiko Arai, Tokyo (JP)

(73) Assignee: Kabushiki Kaisya Advance, Tokyo (JP)

( * ) Notice: Subject to any disclaimer, the term of this patent is extended or adjusted under 35 U.S.C. 154(b) by 0 days.

(21) Appl. No.: 09/308,607

(22) PCT Filed: Nov. 25, 1997

(86) PCT No.: PCT/JP97/04288

§ 371 (c)(1),
(2), (4) Date: May 20, 1999

(87) PCT Pub. No.: WO98/23556

PCT Pub. Date: Jun. 4, 1998

(30) Foreign Application Priority Data

Nov. 25, 1996 (JP) .............................................. 8-328012
Jul. 11, 1997 (JP) .............................................. 9-201033

(51) Int. Cl.$^7$ .................................................. A61K 9/14
(52) U.S. Cl. ..................................................... 424/489
(58) Field of Search ............................... 424/400, 489, 424/497

(56) References Cited

U.S. PATENT DOCUMENTS

| 4,596,574 A | * | 6/1986 | Urist ............................ 623/16 |
| 4,693,986 A | * | 9/1987 | Vit et al. ....................... 501/1 |
| 4,975,415 A | | 12/1990 | Gusman et al. ................ 505/1 |
| 5,019,400 A | * | 5/1991 | Gombotz et al. ........... 424/497 |

FOREIGN PATENT DOCUMENTS

| DE | 38 35 728 | 4/1990 |
| DE | 279 010 | 5/1990 |
| DE | 41 18 752 | 12/1992 |
| EP | 0 376 331 | 7/1990 |
| EP | 0 579 587 | 1/1994 |
| JP | A 59 88351 | 5/1984 |
| JP | A 59 101145 | 6/1984 |
| JP | A 59 182263 | 10/1984 |
| JP | A 60 106459 | 6/1985 |
| JP | A 60 256460 | 12/1985 |
| JP | A 60 256461 | 12/1985 |
| JP | 63-159313 | 7/1988 |
| JP | A 64 75030 | 3/1989 |
| JP | A 1 314572 | 12/1989 |
| JP | 02129031 | 5/1990 |
| JP | A 3 131580 | 6/1991 |
| JP | 4-1122 | 1/1992 |
| JP | 4-2355 | 1/1992 |
| JP | 06293574 A | 10/1994 |

* cited by examiner

Primary Examiner—Thurman K. Page
Assistant Examiner—Robert M. Joynes
(74) Attorney, Agent, or Firm—Christie, Parker & Hale, LLP (57) ABSTRACT

Spherical-shape ceramics obtained by dropping starting ceramics into a low temperature medium or composite spherical-shape ceramics having a composite layer obtained by applying a hydrothermal treatment thereto.

13 Claims, 12 Drawing Sheets

METHOD OF PRODUCTION OF CERAMICS

TECHNICAL FIELD

The present invention relates to a process for producing ceramics, more specifically relates to a process for producing porous ceramics suitable for use as a bone filler or a DDS carrier. The present invention further relates to composite spherical-shape ceramics suitable for use as a medical or dental bone filler or bone cement or other bioceramic material or various resorbable carriers etc.

BACKGROUND ART

In the past, as ceramics having superior biocompatibility, in the field of bone fillers and bone cement, calcium phosphate has been broadly used. The forms at the time of use have mostly been splinter-powder (break to powder), blocks, porous substances, self-setting cements, etc. In particular, in bone fillers, some splinter-powder (break to powder) and blocks have been commercialized.

As an example of application of calcium phosphate, recently attention has been made to the use for DDS carriers. For example, Japanese Unexamined Patent Publication (Kokai) No. 60-106459 discloses a process for producing a sustained drug release type carrier comprising coating combustible beads with calcium phosphate and then sintering them to cause the combustible beads to burn away and leave hollow beads of calcium phosphate, then filling a drug into the hollow portions. Further, Japanese Unexamined Patent Publication (Kokai) No. 59-101145 discloses a process for producing a carrier having a similar effect by impregnating a drug into porous calcium phosphate having open pores.

However, in the above processes, the production steps, such as the injection of the drug into the hollow beads, becomes complicated. Further, it is difficult to control the rate of sustained release of the drug. In the latter process as well, similarly there is a concern over problems such as the complexity of the production steps and the difficulty of control of the rate of sustained release.

On the other hand, spherical-shape calcium phosphate is used as a column filler for liquid chromatography. The general production process is a spray drying granulation method. The spray drying granulation method is generally used for the production of particles having a particle size of 100 µm or less. An extremely large-sized apparatus is required when producing larger particles. Further, as a process for producing spherical-shape calcium phosphate having a size of 100 µm or more, Japanese Unexamined Patent Publication (Kokai) No. 64-75030 discloses a process comprising injecting a ceramics slurry into an oil phase to form a water-in-oil emulsion, then injecting this again into a water phase to solidify the oil phase, followed by sintering to burn off the oil phase, whereby spherical-shape calcium phosphate is obtained.

However, for use as a bone filler, particles having a size of 100 µm or more are desirable. Capital investment is required for producing this by the spray drying granulation method, and therefore, the costs are increased. Further, in the process disclosed in Japanese Unexamined Patent Publication (Kokai) No. 64-75030, production steps for adjusting the oil phase etc. become necessary, and therefore, there are again concerns of increased cost.

An application for DDS requires a superior drug carrying property, biocompatibility, sustained drug release, and biodegrarative. Calcium phosphate is superior in biocompatibility and resorption in the living body or organism. In the past, considerable research went into its application for DDS, but nothing has been commercialized yet. One of the reasons is that, since it is ceramics, it is hard to process. Porosity has to be imparted in order to carry a drug, but it is difficult to change conditions such as the size, strength, distribution of pores, etc. Further, from the viewpoint of the rate of filling in the diseased location or operability, it is desirable that DDS carriers and bone fillers be spherical. Since it is extremely difficult to process ceramics into spheres, this has not yet been commercialized.

Spherical-shape particles have applications in a broad range of fields such as processing powders and carrying catalysts, so that the spherical-shape particles which can be supplied to these fields, it is particularly preferable or sought to produce them in a manner enabling the particle size to be changed in depending upon the order and to enable the particles themselves to functionally carry various substances.

In the medical field, the properties of the particles themselves have come under focus along with the development of drug delivery systems which use particles to carry a drug and effectively release the drug at the desired location in the organism.

Further, in biomaterials as well, calcium phosphate is being broadly used in the fields of bone fillers and bone cement as ceramics superior in biocompatibility. The shapes at the time of use are mostly splinter-powder (break to power), blocks, porous substances, self-setting cement, etc. In particular, in bone fillers, some splinter-powder (break to powder) or blocks have been commercialized.

Japanese Unexamined Patent Publication (Kokai) Nos. 3-131580 and 1-314572 disclose processes of preparation of a porous block of calcium phosphate ceramics. In these processes, it is necessary to shape the block at the time of surgery to match the shape of the bone loss. Further, the implanted block member is often scattered or ejected from the organism before the fusion with the newly grown bone.

To overcome this problem, that is, to cause the granules to fix with each other, Japanese Unexamined Patent Publication (Kokai) Nos. 60-256460 and 60-256461 attempt to use a fibrin paste as a glue. However, a fibrin paste is produced from human blood, therefore had the risk of infection by hepatitis, AIDS, etc.

Further, Japanese Unexamined Patent Publication (Kokai) No. 59-88351 and No. 59-182263 disclose processes for producing a bone repair cement having α-tricalcium phosphate or tetracalcium phosphate as its main ingredient. In these processes, the cement cures at the bone loss portion, then fixes to it densely, so osteoblasts and other tissue and cells will not enter the inside of the filler such as with a porous block. Therefore, the bone substitution ability of a calcium phosphate porous block is superior.

The conventional granular bone filler or porous calcium phosphate block often scatters before fusion with the newly grown bone when implanted in a bone loss portion. Further, the bone cement is inferior in bone substitution capability compared with a porous calcium phosphate bone filler due to the fact that it fixes densely after curing. Therefore, a granular bone filler or porous calcium phosphate block capable of achieving anchoring or preventing scattering at the bone loss portion is preferred. No bone filler having both the functions of a bone filler and bone cement has yet been commercialized.

DISCLOSURE OF THE INVENTION

Accordingly, an object of the present invention is to provide a technique for easily processing a hard-to-process calcium phosphate ceramics into a spherical shape, whereby an effective means of treatment of cancer or bone tumors by impregnation of a drug and administration to the diseased portion is provided, since the spherical-shape ceramics has pores and a resorption in the organism optimal for DDS.

Another object of the present invention is to enable the simple and easy production of spherical-shape ceramics having a functional composite layer having a porous inside and having an outer periphery with different physical properties from the inside, more particularly, to provide a bone filler which enables fusion with newly grown bone or bone substitution action quickly in a natural manner, without scattering, when filled in a bone loss portion and a process of production of the same.

In accordance with the present invention, there is provided a process for producing ceramics by dropping starting ceramics into a low temperature medium, followed by freeze drying and, then sintering.

In accordance with the present invention, there is further provided composite spherical-shape ceramics having a composite layer obtained by dropping a starting material powder into a low temperature medium applying a hydrothermal treatment to the resultant spherical-shape ceramics.

BRIEF DESCRIPTION OF THE DRAWINGS

The present invention will now be explained in detail with reference to the drawings.

BEST MODE FOR CARRYING OUT THE INVENTION

A first embodiment of the present invention will now be explained.

Calcium phosphate synthesized by a known synthesis method, preferably wet synthesis or dry synthesis, preferably hydroxyapatite, tricalcium phosphate, calcium dihydrogenphosphate, tetracalcium phosphate, octacalcium phosphate, calcium phosphate glass, or mixtures thereof calcium phosphates, more preferably tricalcium phosphate, is made into a powder, preferably not more than 100 microns, using a pulverizer or spray dryer etc. Into this powder is added, stirred, and mixed a binder slurry, preferably, an aqueous solution of one or more of a water-soluble cellulose derivative, polyvinyl alcohol, polyacrylic acid, polyacrylamide, polyvinyl pyrrolidone, polyethylene glycol, and starch, more preferably a 3 to 15% by weight aqueous solution of polyvinyl alcohol or polyethylene glycol in an amount of 1 to 5 times, preferably 2 to 4 times, of the weight of the powder. At this time, a similar result can be obtained even if using a 10 to 50% by weight slurry of calcium phosphate other than the powder.

As the ceramics in the present invention, in addition to the above-mentioned calcium phosphate ceramics, alumina, zirconia, carbon, etc. may be mentioned.

The above-mentioned binders are merely examples. In addition, additives may sometimes be added depending upon the mode of use etc., for example, a glycol may be added as a stabilizing agent. Further, if not a porous state, the binder may not be necessary.

The calcium phosphate slurry obtained containing a binder is filled into a cylinder and is dropped from a thin tube attached to the front end of the cylinder, preferably having an inner diameter of 0.3 to 2 mm, into a low temperature refrigerant solution prepared in advance and having a temperature of about −10° C. or less, preferably, liquid nitrogen, liquid helium, acetone+dry ice, methanol+dry ice, or ethyl ether+dry ice.

The dropped calcium phosphate slurry containing the binder becomes spherical shape during its fall and at the surface of the liquid nitrogen and can be frozen, while maintaining the spherical shape.

The frozen slurry obtained is freeze-dried so as not to thaw and to completely remove the moisture. The spherical-shape calcium phosphate thus obtained is sintered using an electric furnace at 800° C. to 1500° C., preferably 1000° C. to 1400° C., to obtain the spherical-shape ceramics.

The diameter of the ceramics powder obtained by this production process is 0.01 to 10 mm, but can be adjusted in various ways by the mode of contact such as the dropping conditions.

In the present invention, it is sufficient to bring the ceramics solution into contact with a low temperature refrigerant. Various modes of contact are possible, but other than the dropping, spraying by an atomizer such as a spray dryer, pressurized spraying by a spray, contact with a container in by injection, pouring, and other means of introduction into a container, etc. may be mentioned.

The spherical-shape ceramics has fine pores formed at the time of evaporation of the binder over the spheres as a whole. A drug etc. may be impregnated into the ceramics from these pores. Further, the diameter of the pores may be varied by the content of the binder. Further, since the pores can be plugged by a known calcium phosphate cement or other synthetic resin etc., control of the rate of sustained release is possible.

Due to the uniform porosity, the sustainability of the sustained release in the orgnism is, for example, units of several days or several weeks in the body fluids, more specifically for one week to three weeks. A similar sustainability can be obtained in the body tissue as well.

Therefore, by filling this spherical-shape ceramics into a portion of bone loss, since the pores, one of the features of this spherical-shape ceramics, do not block the flow of blood, it is possible to quickly regenerate the bone. Further, the effect can be enhanced further by impregnating the pores with bone-growth factors, collagen, antibiotics, and other drugs.

The present invention, in addition to the above, may be used as a main material or additive etc. for various products such as orally administered drugs, processed foods, beverages, various adsorption column materials, cosmetics, dentifrices, fumigants, air fresheners and deodorizing agents, bath additives, facial cleansers, shampoos, and other toiletries, fibers having adsorption or other functions or paper materials and other fields requiring adsorption and sustained release of the carried substances.

In this above way, a good sustained release drug can be obtained by carrying various drugs. Due to the superior sustained release, for example, penicillin type antibiotics, tetracycline type antibiotics, the anticancer drugs 5FU, carboplatin, cisplatin, etc. are preferably used.

The specific production process of composite spherical-shape ceramics according to the second aspect of the present invention comprises mixing a binder into a high purity calcium phosphate powder obtained by a known synthetic method, preferably wet synthesis and dry synthesis, preferably a hydroxyapatite, tricalcium phosphate, or tetracalcium phosphate, then shape the mixture by any method and sinter it at a temperature of 800 to 1500° C. to obtain a calcium phosphate ceramics superior in biocompatibility. As the method of shaping, a monoaxial press, rubber press, etc. may be used for easy shaping. Further, by mixing a burn-off substance in the binder, it is possible to make the ceramics porous after sintering. Porous ceramics facilitate the entry of osteoblasts and other tissue in the organism and a bone regenerating capability to be exhibited more suitably, when implanted in a bone loss portion. However, since the dynamic strength is poor, it is necessary to pay close attention at the time of use.

The porous or dense calcium phosphate ceramics obtained, and a suitable amount of ion exchange water are placed in a heat resistant sterile bottle and heated in a sealed atmosphere at 80° C. to 150° C., preferably 100° C. to 120° C., for at least 30 minutes, preferably 12 to 24 hours to cause high purity calcium phosphate crystal to precipitate on the surface of the ceramics (hereinafter this technique is called "hydrothermal treatment"). The crystal is comprised of the phosphoric acid and calcium eluted from the surface of the sintered product reprecipitating on the surface of the ceramics. Therefore, an extremely high purity calcium phosphate crystal precipitates over the entire surface of the ceramics. The particles of ceramics grow by the sintering and the specific surface area rapidly drops. However, by using the above process to cause crystals to precipitate on the surface, the specific surface area can be restored to a certain extent again. By increasing the specific surface area, it is possible to obtain an anchoring effect in the organism even if used as a bone filler in this state.

The hydrothermal treatment in the present invention may be performed by causing crystal to precipitate in steam using an autoclave in addition to the above technique. More specifically, this consists of heating the mixture under a sealed steam atmosphere in an autoclave at 80° C. to 150° C., preferably 100° C. to 120° C., for at least 30 minutes, preferably 12 to 24 hours so as to cause high purity calcium phosphate crystal to precipitate on the surface of the ceramics. Further, in the process using a heat resistant sterilize bottle or the process using an autoclave, it is possible to reduce the hydrothermal treatment time and control the precipitated layer by using an aqueous solution for impregnated with the ceramics and an aqueous solution containing calcium, phosphate, or other ions in a steam atmosphere.

In this hydrothermal treatment, the width of the precipitated layer is controlled by the treatment time, amount of pressure, pressurizing temperature, treatment atmosphere, etc. Specifically, it may be suitably selected depending upon the application such as the bone filler, DDS carrier, dental root canal filler, ceramics adsorbent, column chromatography filler, or other application.

The coating method of a cement on the surface of a bone filler, without impairing, the setting (or curing) function, to enhance the anchoring effect is explained below. The calcium phosphate ceramics with crystal precipitated on the surface thereof is mixed with a bone cement which cures by kneading with water and a setting (or curing) solution. As the bone cement, α-tricalcium phosphate, tetracalcium phosphate, octacalcium phosphate, calcium sulfate, or any mixture thereof is preferable as the cement.

Further, the present invention is not limited in biomaterials. Any fine particles having the composite layer, in particular porous fine particles, which can be made to carry various substances in the porous portions are particularly preferred.

After mixing, a suitable amount of ion exchange water is added and quickly kneaded. The cement is instantaneously frozen in liquid nitrogen, liquid helium, or another super-low temperature medium or super-low temperature atmosphere before the cement completely sets (or cures). A bone cement has a large specific surface area. The crystal growth starts by a hydrolysis reaction when moisture adheres to the cement surface. By mixing and kneading this with a cement material, the bone cement in the intervals of the crystals precipitated on the surface of the ceramics can stop the crystal growth due to the setting by the instantaneous freezing. The instantaneously frozen bone cement and bone filler are then freeze-dried. The freeze-drying can completely remove the moisture while maintaining the specific surface area of the cement to a certain extent. Therefore, it is possible to separate the dried product obtained into the bone filler and cement, then cause it to function as cement again.

Bone cement is taken into the intervals of the crystal reprecipitated on the surface of the bone filler. The bone cement taken in secures the specific surface area required for setting due to the freeze-drying. Therefore, the bone filler according to the present invention is a bone filler coated on the surface thereof with a setting type bone cement. When implanted in a bone loss portion, it can bond with the portion by the setting action of the surface and effectively prevent the bone filler from scattering after implantation. Further, by making the core ceramics porous, there is the same bone substitution ability as a granular porous filler.

As explained above, as the drug carried, a broad range of drugs can be used. Further, since the surface is treated by reprecipitation, the rate of dissolution in the organism is adjusted, therefore the function becomes extremely marked.

A good sustained release drug is obtained by carrying various drugs. Due to the superior sustained release, for example, penicillin type antibiotics, tetracycline type antibiotics, the anticancer drugs 5FU, carboplatin, cisplatin, acrarubicin hydrochloride, daunorubicin hydrochloride, neocartinostatin, acutinomycin D, pepromycin sulfate, piralbicin hydrochloride, doxorubicin hydrochloride, bleomycin hydrochloride, bleomycin sulfate, mitomycin, and other drugs may be suitably used.

In the second embodiment of the present invention as well, in addition to the above, the present invention may be used as a main material or substrate etc. for various products such as orally administered drugs, processed foods, beverages, various adsorption column materials, cosmetics, dentifrices, fumigants, air fresheners and deodorizing agents, bath additives, facial cleansers, shampoos, and other toiletries, fibers having adsorption or other functions or paper materials and other fields requiring adsorption and sustained release of the carried substances.

EXAMPLES

The present invention will be explained in more detail with reference to Examples, but the present invention is of course not limited to these Examples in scope.

Example I-1

1 g of calcium phosphate powder (#400 mesh or less) having Ca/P=1.48 synthesized by a known wet synthesis method was mixed into 3 g of a 10% by weight aqueous solution of polyvinyl alcohol, then 0.5 g of ion exchange water was added and the mixture further mixed and stirred. 10 ml of the slurry obtained was filled into a thermosyringe and a 24 G needle (inner diameter 0.47 mm) was used to drop it into liquid nitrogen. The frozen product obtained was dried using a vacuum freeze dryer, then was sintered at 1400° C. for 5 hours to obtain 0.9 g of spherical-shape ceramics. The spherical-shape frozen product obtained has a diameter of 0.8 to 1.2 mm. Powder X-ray measurement confirmed that the spherical-shape ceramics was a single phase of α-tricalcium phosphate.

Example I-2

The spherical ceramics prepared in Example I-1 was observed by a scanning-type electron microscope (SEM). The sample was observed by two types of methods: the surface of the sample and the sliced section of the sample. As a result, the surface of the sample was observed to have pores of 1 to 4 μm distributed over its entire surface. Further, the SEM image of the sliced section showed that there were pores of 100 to 200 μm inside the spherical-shape ceramics. It was confirmed that there was a mozaic structure of calcium phosphate around it. (See FIGS. 1(a) and 1(b) and FIGS. 2(a) and 2(b).)

Example I-3

The spherical ceramics prepared in Example I-1 was immersed in red ink, then deaerated under vacuum for about 10 minutes. This was returned to ordinary pressure, then the excess ink was wiped off and the sample dried by freeze-drying in vacuum. The sample was sliced at its center portion, whereupon it was confirmed that the red ink had penetrated to the inside of the ceramics. Therefore, it is possible to easily impregnate a drug by just a short period of vacuum deaeration.

Example I-4

Figure 1A:
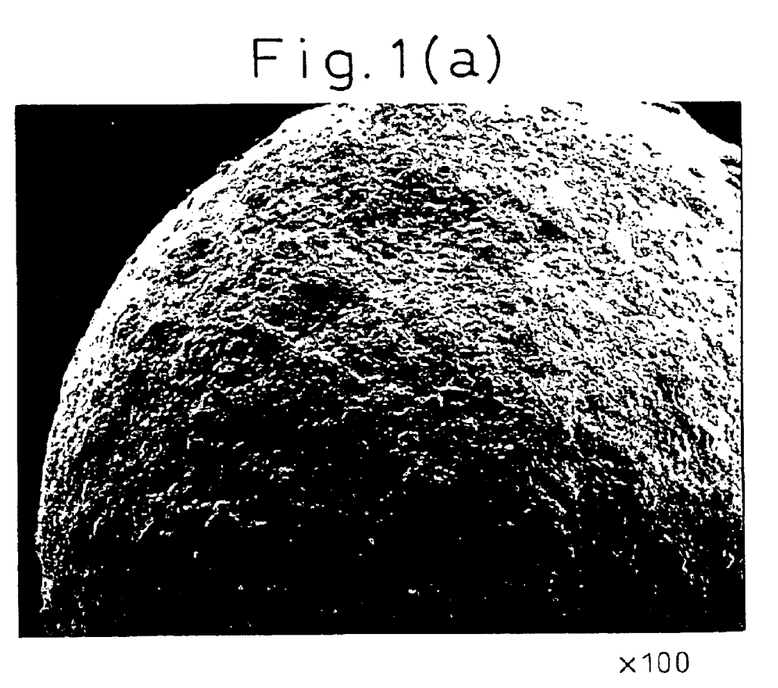
FIGS. 1(a) and 1(b) are scanning-type electron micrographs of the surface of porous ceramics powder shown in Example I-2 (100x and 1000x, respectively).
Figure 1B:
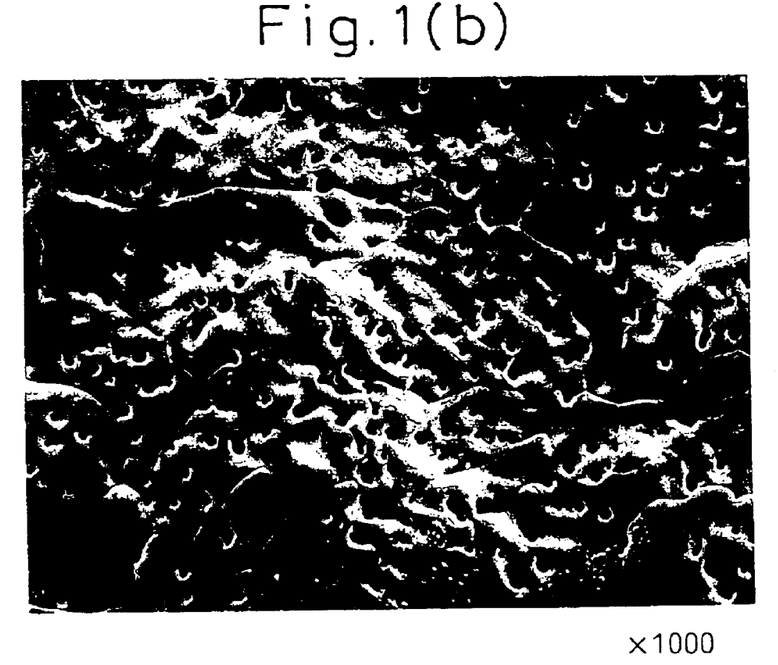
Figures 2A, 2B:
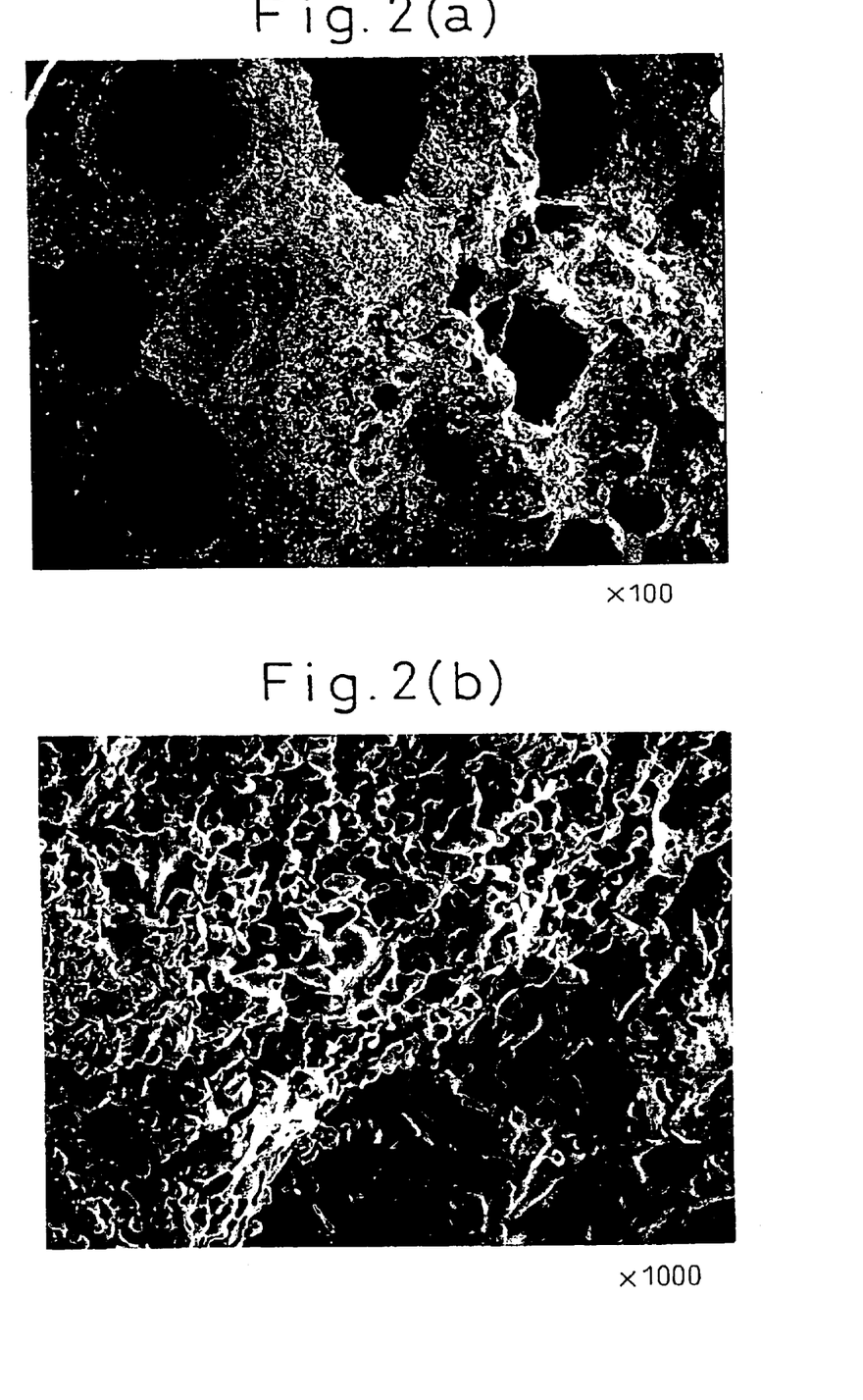
FIGS. 2(a) and 2(b) are scanning-type electron micrographs of the sliced cross-section of porous ceramics powder shown in Example I-2 (100x and 1000x, respectively).
Figure 3A:
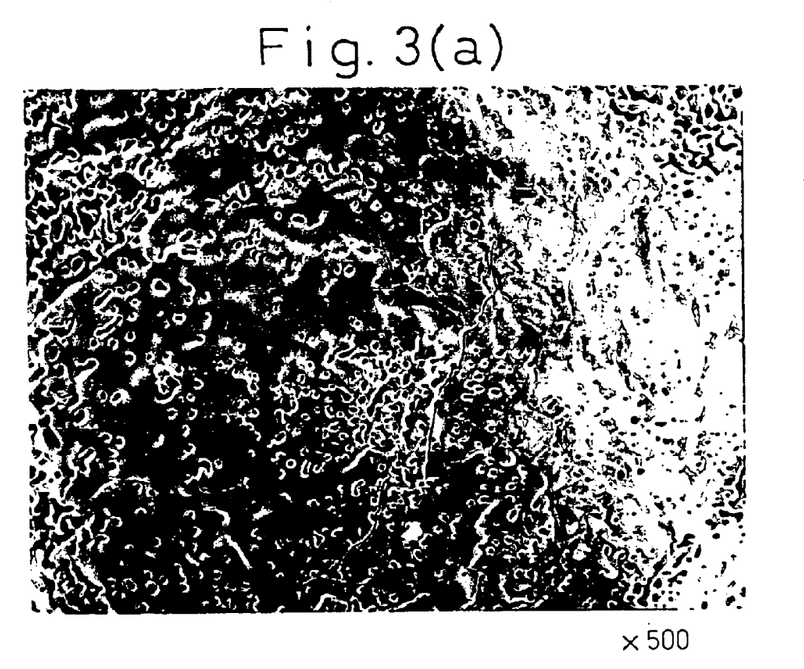
FIGS. 3(a), 3(b), 3(c), 3(d), 3(e), 3(f), 3(g), 3(h), 3(i), and 3(j) are scanning-type electron micrographs showing the mode of dissolution along with time of the porous ceramics shown in Example I-4 in ion exchange water.
Figure 3B:
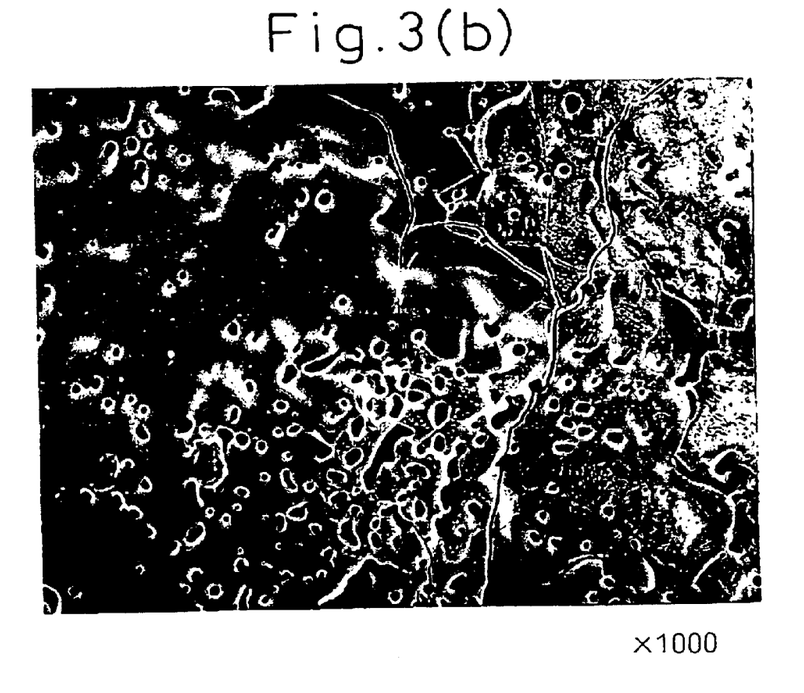
Figure 3C:
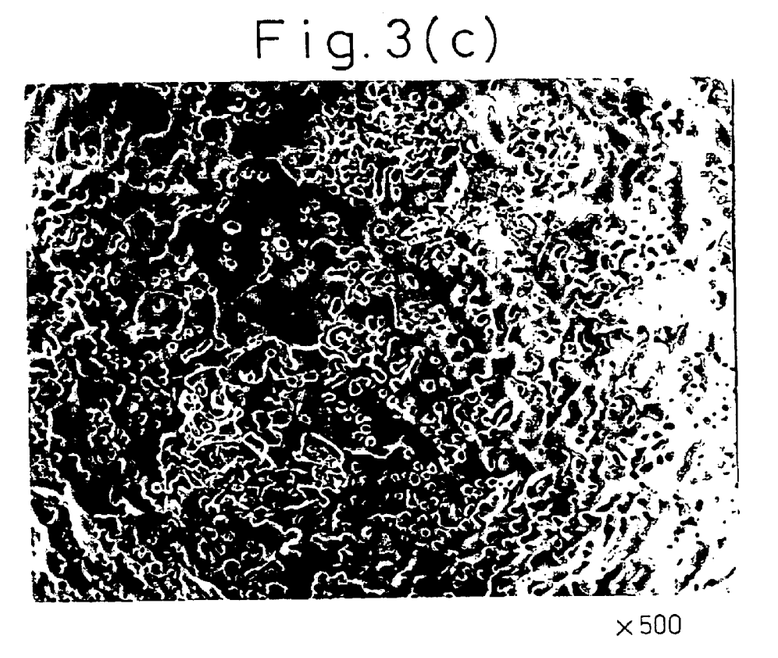
Figure 3D:
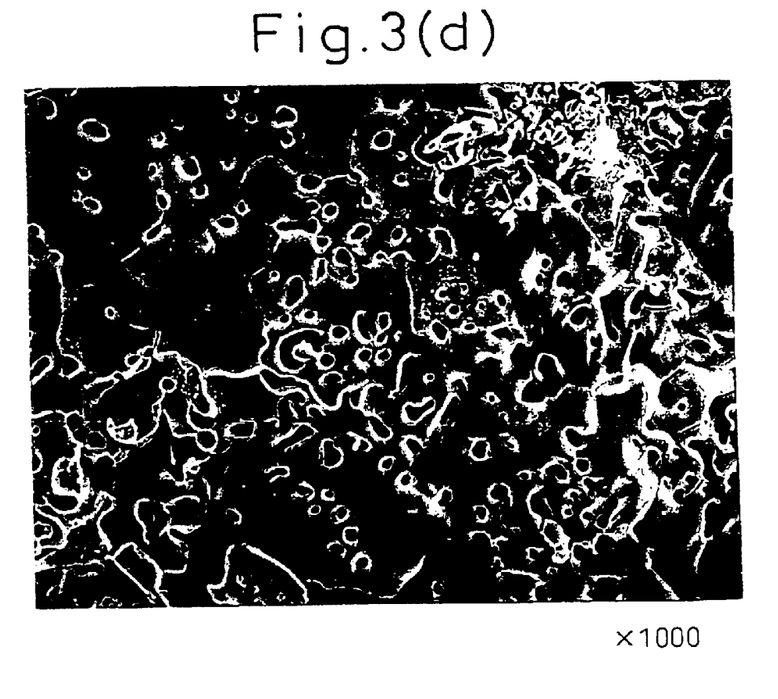
Figure 3E:
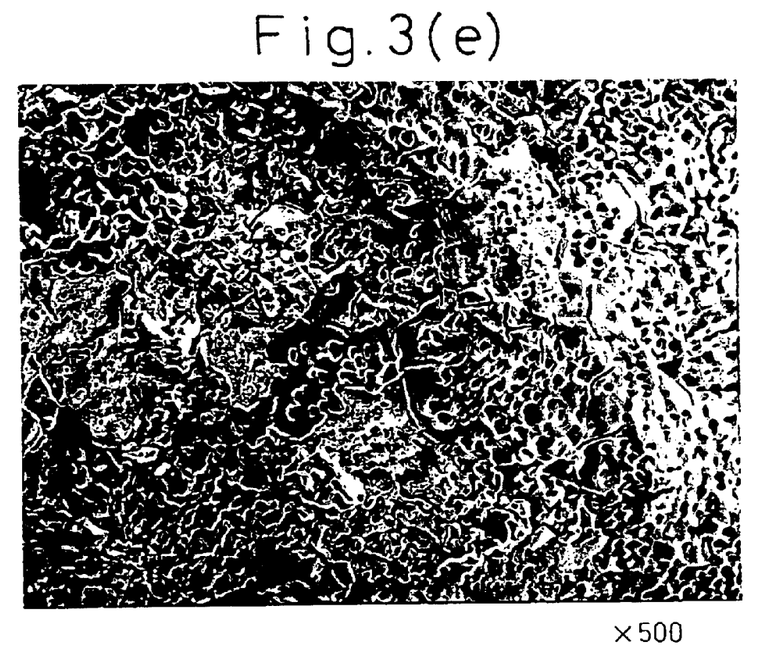
Figure 3F:
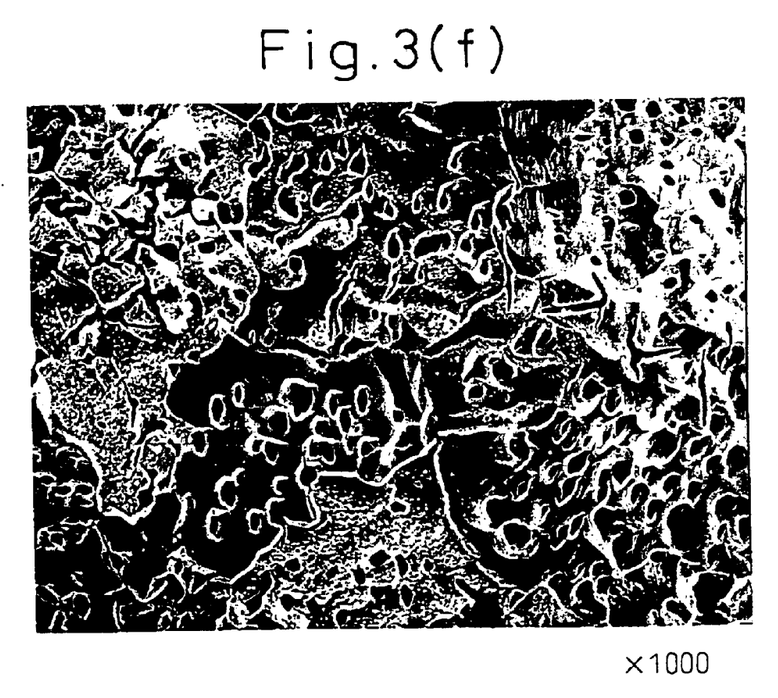
Figure 3G:
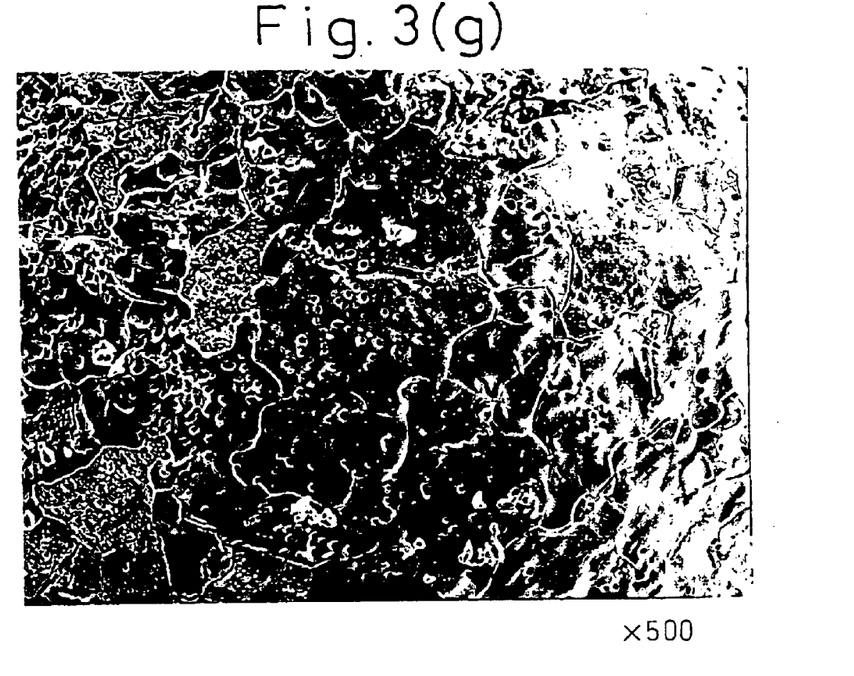
Figure 3H:
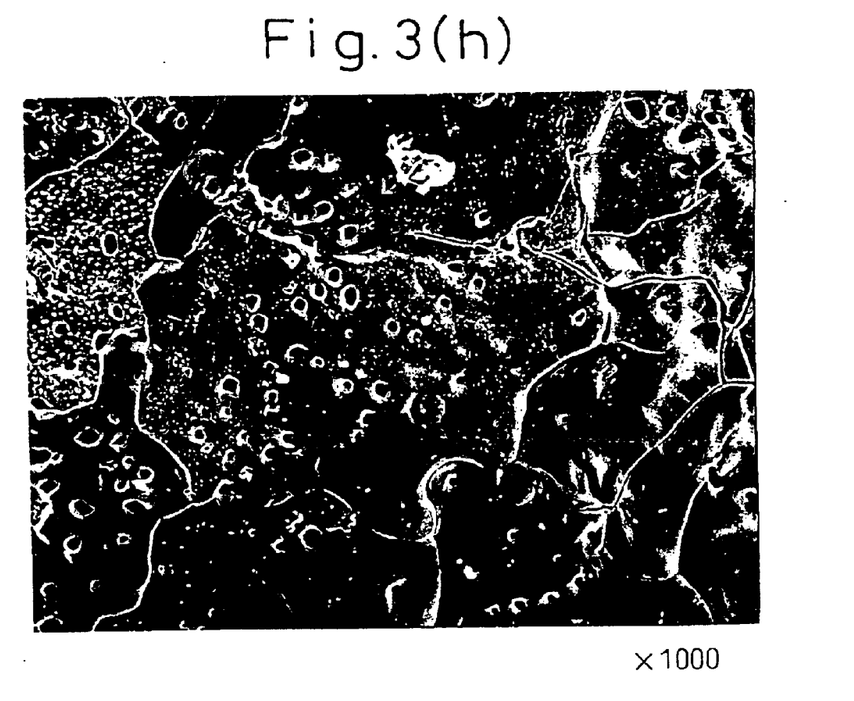
Figure 3I:
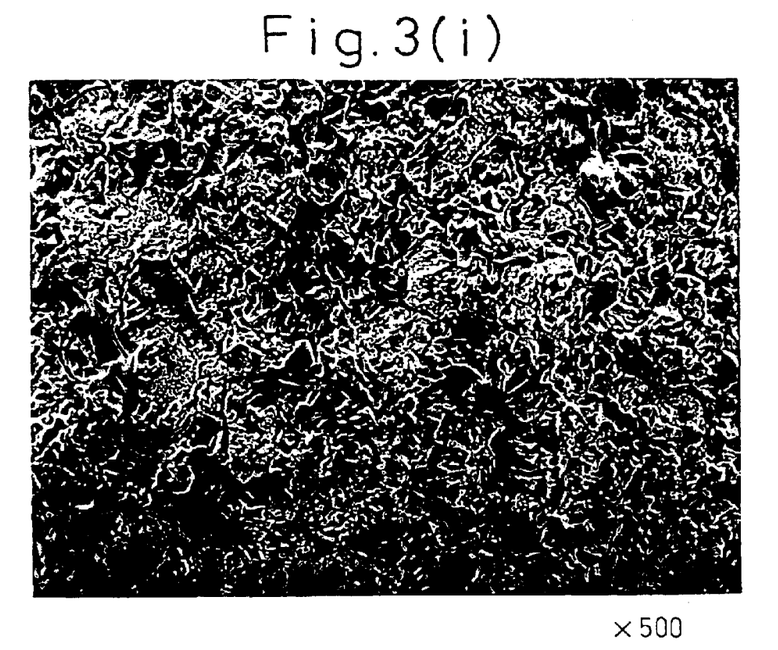
Figure 3J:
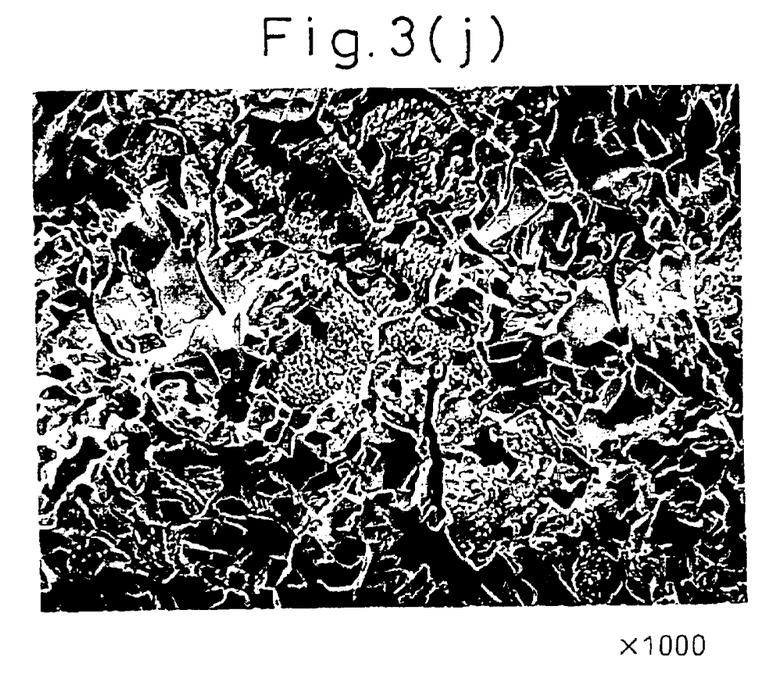
Figure 4A:
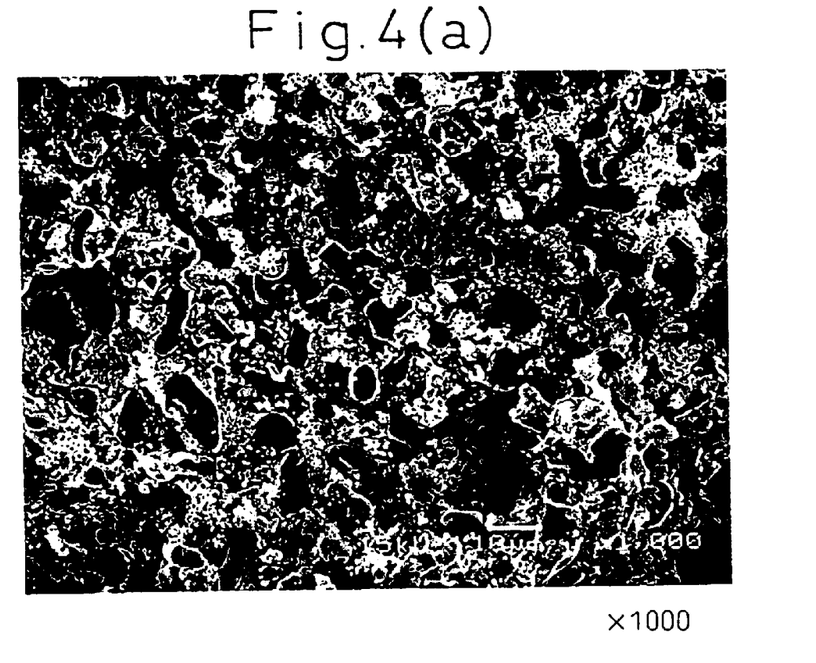
FIGS. 4(a) and 4(b) are scanning-type electron micrographs of the frozen sliced cross-section of porous ceramics shown in Example I-5 (1000x and 3000x, respectively).
Figure 4B:
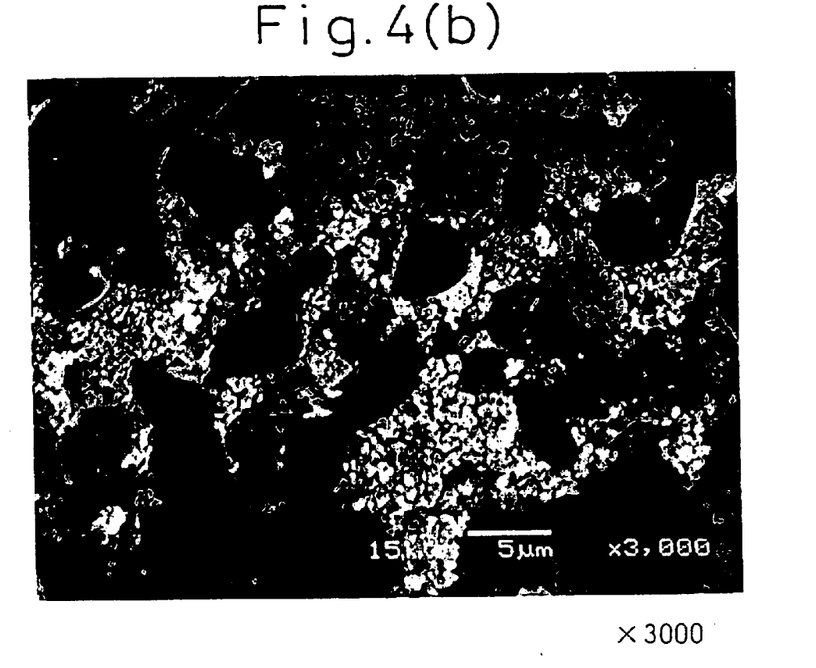

The spherical-shape porous ceramics prepared in Example I-1 was immersed in 50 ml of ion exchange water for 1 hour, 1 day, 3 days, 7 days, and 14 days and the form of dissolution was observed over time by a scanning-type electron microscope. The obtained electron micrographs are shown in FIGS. 3(a) (1 hour, 500x), 3(b) (1 hour, 1000x), 3(c) (1 day, 500x), 3(d) (1 day, 1000x), 3(e) (3 days, 500x), 3(f) (3 days, 1000x), 3(g) (7 days, 500x), 3(h) (7 days, 1000x), 3(i) (14 days, 500x), and 3(j) (14 days, 1000x). The sample was a spherical-shape porous ceramics for a drug carrier superior in resorption in the body.

As a result, it was confirmed that the spherical-shape porous ceramics quickly dissolved and the state of dissolution occurred with units of clump of grain peeling off in a plate shape. A similar trend may be seen in the body as well. This material was shown to be a material which is finally completely resorbed while releasing the drug.

Example I-5

The spherical-shape porous ceramics prepared in Example I-1 was immersed in a dispersion of fine hydroxyapatite particles and subjected to ultrasonic waves, while being vacuum deaerated. Then, the sample was frozen and sliced and observed under a scanning-type electron microscope.

Figure 6A:
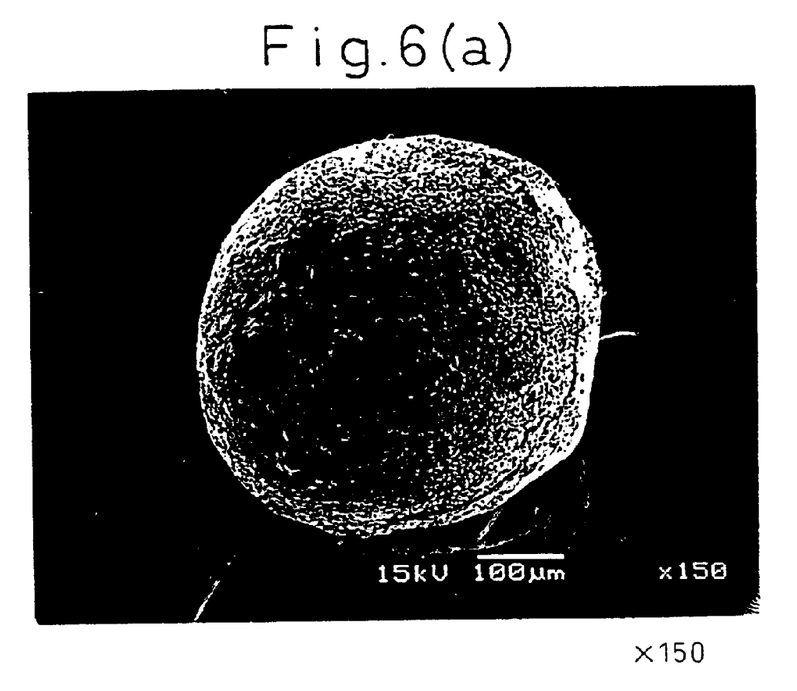
FIGS. 6(a) and 6(b) are scanning-type electron micrographs after immersion in a refrigerant in the production process of the spherical-shape ceramics of the present invention (150x and 1000x, respectively).
Figure 6B:
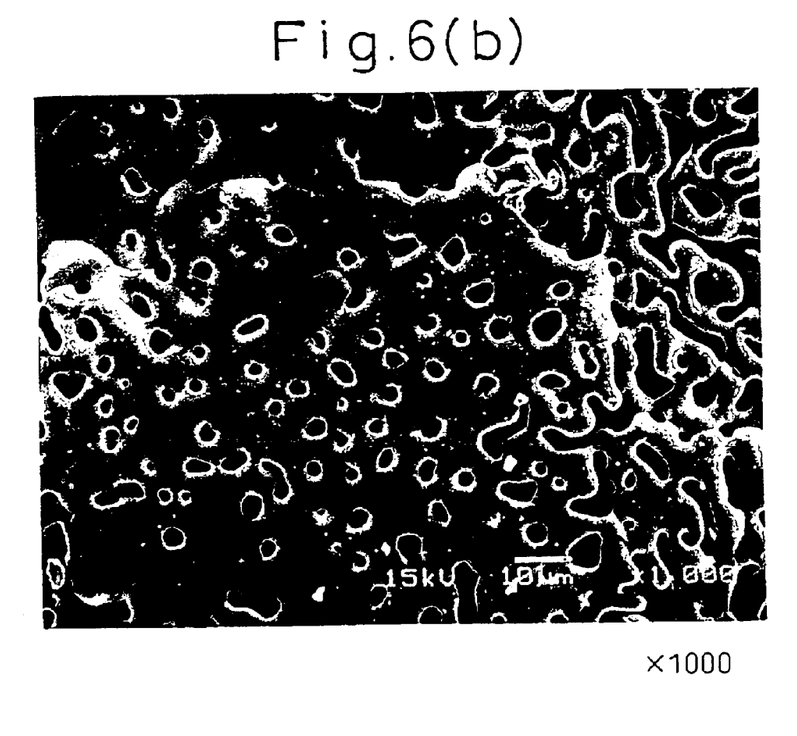

1 g of calcium phosphate powder (#400 mesh or less) having Ca/P=1.48 synthesized by a known wet synthesis method was mixed into 3 g of a 10% by weight aqueous solution of polyvinyl alcohol, then 0.5 g of ion exchange water was added and the mixture further mixed and stirred. 10 ml of the slurry obtained was filled into a thermosyringe and a 24 G needle (inner diameter 0.47 mm) was used to drop it into liquid nitrogen. The frozen product obtained was dried using a vacuum freeze dryer, then was sintered at 1400° C. for 5 hours to obtain 0.9 g of spherical-shape ceramics. The spherical-shape frozen product obtained has a diameter of 0.8 to 1.2 mm. (See FIGS. 6(a) and 6(b).)

Example I-6

As a simulation experiment for confirming the sustained drug release effect, 10% by weight of fine hydroxyapatite particles was mixed into a 10 mM aqueous Methyl orange solution and stirred well. This was filled into the fine pores of the spherical-shape porous ceramics by the method shown in Example I-5. 0.2 g of the sample filled in the fine pores was introduced into 200 ml of ion exchange water, then the immersion solution was taken after a predetermined time and the amount of elution of Methyl Orange was compared by the absorbance by an ultraviolet spectrophotometer. As a control, spherical-shape porous ceramics without the fine pores filled immersed in a 10 mM aqueous Methyl Orange solution was used.

Figure 5:
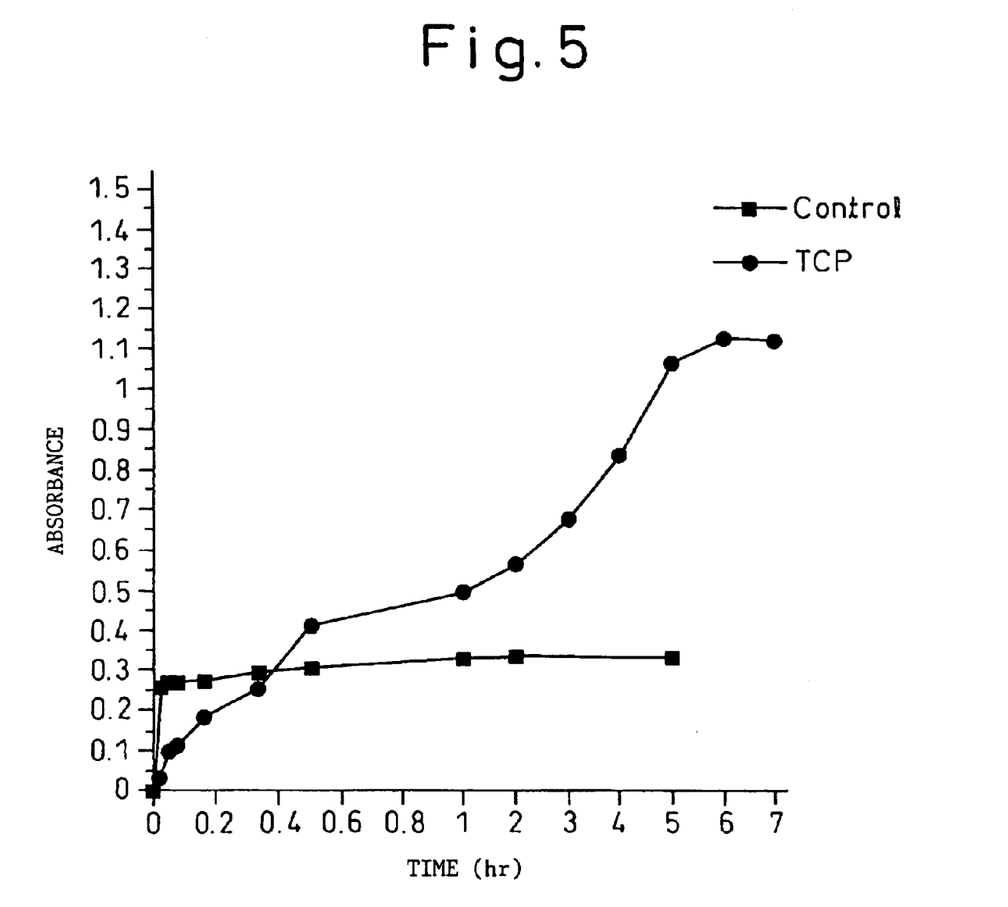
FIG. 5 is a graph of the results of Example I-6.

As a result, it was found that the sample having the filled fine pores carried about three times the amount of Methyl Orange compared with a sample not filled. Further, as a result of the sustained release, the Methyl Orange could be released over an approximately 10 times longer period. The possibility of obtaining excellent therapeutic effects by replacing the Methyl Orange with various types of antibiotics or antitumor preparations was suggested (see FIG. 5).

Example II-1

1 g of calcium phosphate powder (#400 mesh or less) having a Ca/P=1.48 synthesized by a known wet synthesis method was mixed into 3 g of a 10% by weight aqueous solution of polyvinyl alcohol, then 0.5 g of ion exchange water was added and the mixture further mixed and stirred. 10 ml of the slurry obtained was filled into a thermosyringe and a 24 G needle (inner diameter 0.47 mm) was used to drop it into liquid nitrogen. The frozen product obtained was dried using a vacuum freeze dryer, then this was sintered at 1400° C. for 5 hours to obtain 0.9 g of spherical-shape ceramics. The spherical-shape ceramics obtained had a diameter of 0.8 to 1.2 mm. (See FIGS. 6(a) and 6(b).)

Figure 7A:
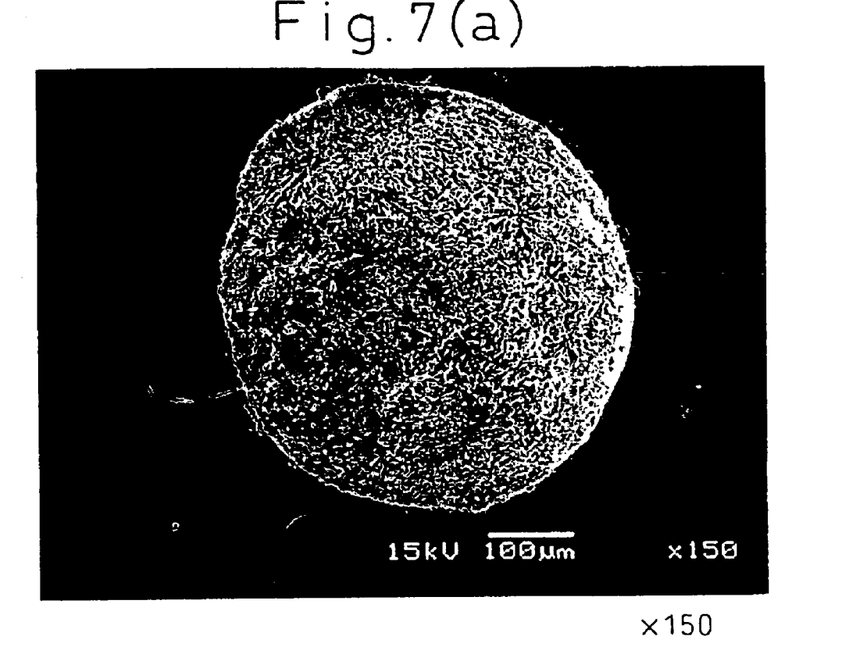
FIGS. 7(a) and 7(b) are scanning-type electron micrographs after the hydrothermal treatment in the process of production of the spherical-shape ceramics of the present invention (150x and 1000x, respectively).
Figure 7B:
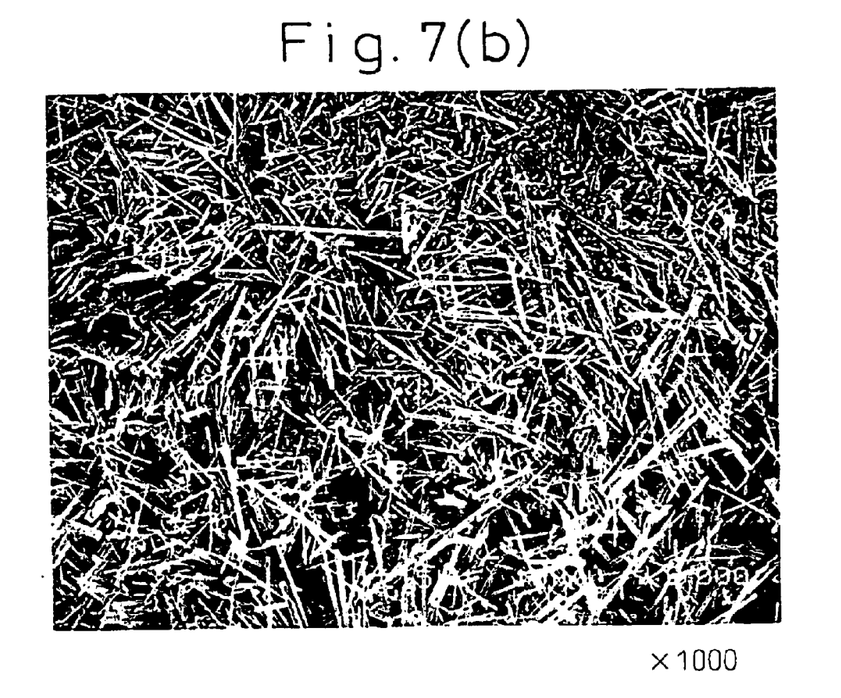

0.9 g of the spherical-shape ceramics obtained was inserted into a heat resistant sterile bottle, then 50 ml of ion exchange water was added and the bottle corked. This was placed in a 120° C. incubator for 1 hour to make calcium phosphate crystal precipitate on the surface of the spherical-shape ceramics. This was dried in the incubator, then the surface condition was observed by a scanning-type electron microscope, whereupon it was confirmed that 10 to 20 μm calcium phosphate crystals were distributed over the entire surface. (see FIG. 7(a) and 7(b).)

Example II-2

Figure 8A:
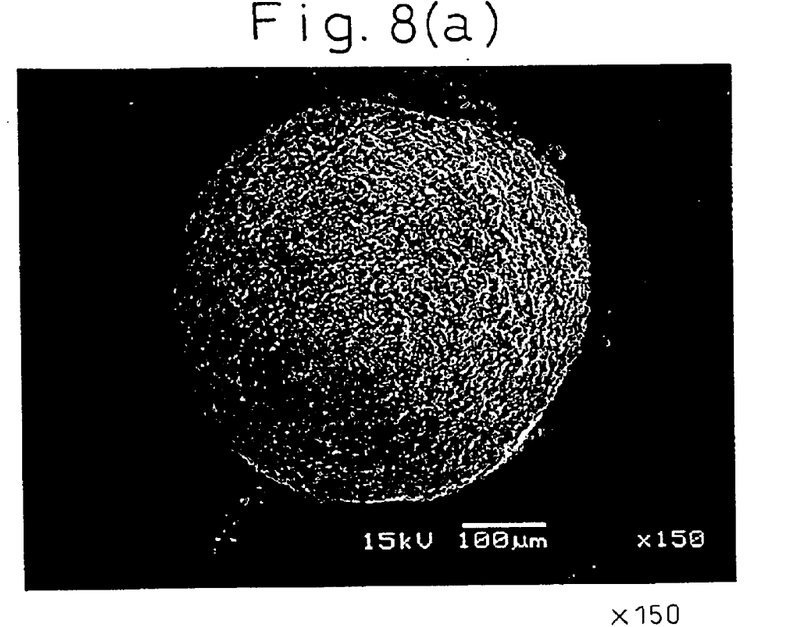
FIGS. 8(a) and 8(b) are scanning-type electron micrographs after cement coating in the process of production of the spherical-shape ceramics of the present invention (150x and 1000x, respectively).
Figure 8B:
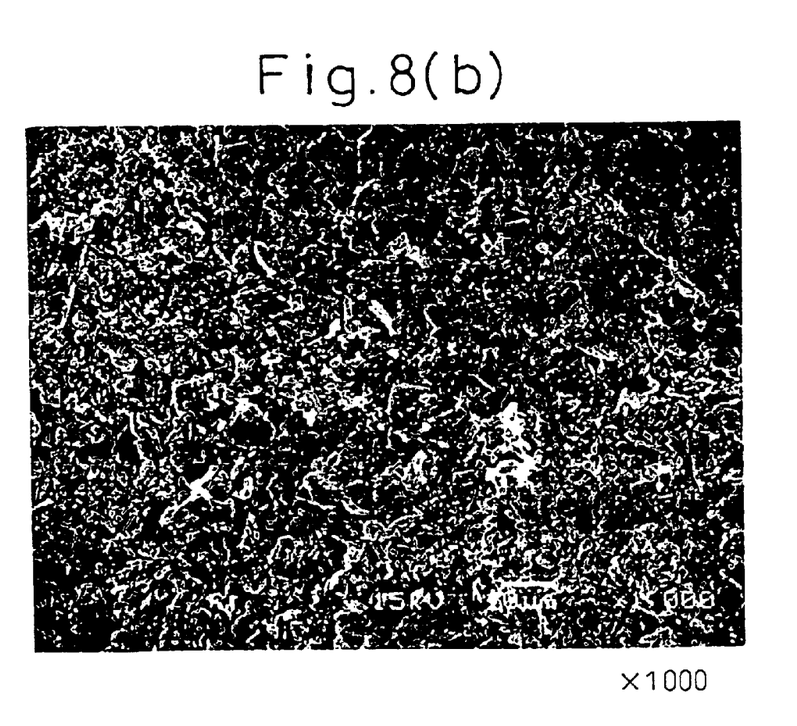

Spherical-shape ceramics on the surface of which calcium phosphate crystal was precipitated, prepared in Example II-1, and calcium sulfate powder were mixed and then a suitable quantity of ion exchange water was added to create a cement-like state. This was kneaded for 1 minute, then the cement was filled into an eggplant-shaped flask which was then immersed in liquid nitrogen to instantaneously freeze the cement. Then, this was quickly dried using a freeze dryer. The dried sample was passed through a rated sieve #100 to remove the surplus deposited calcium sulfate to coat calcium sulfate cement on the surface and obtain a bone filler. (See FIGS. 8(a) and 8(b).)

Example II-3

To investigate the state of curing of the bone filler prepared in Example II-2, a hole of a diameter of about 4 mm was bored into the rib of a hog and the bone filler was filled in the hole. After about 1 hour after filling, the bone filler completely set and it became impossible to withdraw the bone filler from the hole. This experiment confirmed the low possibility of the product of the present invention detaching from the diseased portion when filled in a portion of bone loss.

INDUSTRIAL APPLICABILITY

As explained above, according to the present invention, it is possible to produce ceramics freely controlled in particle size and pore size simply and in a short time. Therefore, when used as a bone filler, there is the effect of promoting bone regeneration, without blocking the flow of blood in the bone. Further, by impregnating a drug in the resorbable ceramics, an ideal sustained drug release carrier is obtained.

According to the present invention, by coating a ceramic cement on the surface of ceramics with a superior biocompatibility, the cement sets by a hydrolysis reaction when implanted at the bone loss portion and anchors the ceramics sintered granules in the bone loss portion. Therefore, while past granular bone fillers had suffered from the problem of scattering from the bone loss portion, this problem has been solved by the present invention.

What is claimed is:

1. A process for producing porous spherically-shaped bio-ceramics comprising dropping a starting material for ceramics into a low temperature medium from a thin tube having an inner diameter ranging from about 0.3 to 2 mm, followed by freeze drying in the medium and then sintering the same, wherein the starting material is obtained by adding, to a calcium phosphate in the form of a powder having a size of not more than 100 μm, a 3 to 15% by weight aqueous solution of a binder in an amount of 2 to 4 times the weight of the powder.

2. A process for producing porous spherically-shaped bio-ceramics as claimed in claim 1, wherein the calcium phosphate is hydroxyapatite, tricalcium phosphate, calcium dihydrogenphosphate, tetracalcium phosphate, octacalcium phosphate, or a mixture thereof.

3. A sustained drug release product obtained by forming the porous spherical-shape bio-ceramics obtained according to claim 1 or 2, wherein the pores are impregnated with a drug.

4. A sustained drug release product as claimed in claim 3, wherein, after the drug is impregnated into the porous bio-ceramics, the impregnated parts are plugged by said bio-ceramics, whereby the sustained release time of the drug is controlled.

5. A process for producing porous spherically-shaped bio-ceramics comprising:

bringing a starting material for bio-ceramics into contact with a low temperature medium by dropping the starting material into the low temperature medium from a thin tube having an inner diameter ranging from about 0.3 to 2 mm, wherein the starting material is obtained by adding, to a calcium phosphate in the form of a powder having a size of not more than 100 μm, a 3 to 15% by weight aqueous solution of a binder in an amount of 2 to 4 times the weight of the powder, followed by freeze drying in the medium to form a freeze dried product and;

thereafter sintering the resultant freeze dried product.

6. A process for producing porous spherically-shaped bio-ceramics as claimed in claim 5, wherein the calcium phosphate is hydroxyapatite, tricalcium phosphate, calcium dihydrogenphosphate, tetracalcium phosphate, octacalcium phosphate, or a mixture thereof.

7. A process for producing a sustained drug release product comprising impregnating the pores of the porous spherical-shape bio-ceramics obtained according to claim 1 or 2 with a drug.

8. A process as claimed in claim 7, wherein, after the drug is impregnated into the porous bio-ceramics, the impregnated parts are plugged by said bio-ceramics, whereby the sustained release time of the drug is controlled.

9. A process as claimed in claim 1, wherein the binder slurry is an aqueous solution of one or more of a water-soluble cellulose derivative, polyvinyl alcohol, polyacrylic acid, polyacrylamide, polyvinyl pyrrolidone, polyethylene glycol, and starch.

10. A filler for regenerating body tissue comprising porous spherically-shaped bio-ceramics obtained by a process according to claim 1.

11. A method for regenerating body tissue comprising introducing into areas where body regeneration is desired porous spherically-shaped bio-ceramics obtained by a process according to claim 1.

12. A process for producing porous spherically-shaped bio-ceramics as claimed in claim 1, wherein the porous spherically-shaped bio-ceramics each have a diameter ranging from about 0.01 to about 10 mm.

13. A process for producing a sustained drug release product according to claim 1 or 5 wherein the low temperature medium is liquid nitrogen.

* * * * *